United States Patent
Müller et al.

(10) Patent No.: US 8,975,448 B2
(45) Date of Patent: Mar. 10, 2015

(54) PROCESS FOR PREPARING 2,2-DIFLUOROETHANOL

(75) Inventors: Thomas Norbert Müller, Monheim (DE); Norbert Lui, Odenthal (DE); Stefan Moczarski, Köln (DE)

(73) Assignee: Bayer Intellectual Property GmbH, Monheim am Rhein (DE)

( * ) Notice: Subject to any disclaimer, the term of this patent is extended or adjusted under 35 U.S.C. 154(b) by 0 days.

(21) Appl. No.: 14/232,170

(22) PCT Filed: Jul. 16, 2012

(86) PCT No.: PCT/EP2012/063898
§ 371 (c)(1),
(2), (4) Date: Apr. 7, 2014

(87) PCT Pub. No.: WO2013/010985
PCT Pub. Date: Jan. 24, 2013

(65) Prior Publication Data
US 2014/0243561 A1    Aug. 28, 2014

Related U.S. Application Data

(60) Provisional application No. 61/509,800, filed on Jul. 20, 2011.

(30) Foreign Application Priority Data

Jul. 19, 2011 (EP) .................................... 11174510

(51) Int. Cl.
*C07C 29/147* (2006.01)
*C07C 67/11* (2006.01)
*C07C 29/128* (2006.01)
*C07C 67/10* (2006.01)
*C07C 31/38* (2006.01)

(52) U.S. Cl.
CPC .............. *C07C 29/147* (2013.01); *C07C 67/11* (2013.01); *C07C 29/1285* (2013.01); *C07C 67/10* (2013.01); *C07C 31/38* (2013.01)
USPC ........................................................ 568/842

(58) Field of Classification Search
USPC ........................................................ 568/842
See application file for complete search history.

(56) References Cited

FOREIGN PATENT DOCUMENTS

| | | |
|---|---|---|
| EP | 1820789 | 8/2007 |
| JP | 62273925 | 5/1986 |
| JP | 62-273925 | 11/1987 |
| WO | 2007071841 | 6/2007 |
| WO | 2009040367 | 4/2009 |

OTHER PUBLICATIONS

International Search Report for PCT/EP2012/063898 Mailed Oct. 12, 2012.
Henne et al., J. Am. Chem. Soc., 1952, 74, pp. 1426-1428.
Booth et al., Tetrahedron 1990, 46, pp. 2097-2110.
Daisuke et al., Effect of Solvent on the Esterification Between 1,1,1-Trifluorochloroethane and Akaline Acetate. Central Research Institute, Mitsubishi Metal Corp., p. 69, (1985).

*Primary Examiner* — Sikarl Witherspoon
(74) *Attorney, Agent, or Firm* — Miles & Stockbridge PC

(57) ABSTRACT

Process for preparing 2,2-difluoroethanol, comprising the following steps: reacting 1-chloro-2,2-difluoroethane with an alkali metal salt of formic acid or acetic acid in a suitable solvent to give the corresponding 2,2-difluoroethyl formate or 2,2-difluoroethyl acetate, and transesterifying the 2,2-difluoroethyl formate or 2,2-difluoroethyl acetate from step (i) in the presence of an alcohol and optionally of a base.

13 Claims, No Drawings

PROCESS FOR PREPARING 2,2-DIFLUOROETHANOL

CROSS REFERENCE TO RELATED APPLICATIONS

This application is a §371 National Stage Application of PCT/EP2012/063898, filed Jul. 16, 2012, which claims priority to European Application No. 11174510.5, filed Jul. 19, 2011, and claims benefit of U.S. Provisional Application No. 61/509,800, filed Jul. 20, 2011.

BACKGROUND OF THE INVENTION

1. Field of the Invention

The present invention relates to a process for preparing 2,2-difluoroethanol proceeding from 2,2-difluoro-1-chloroethane (1-chloro-2,2-difluorethane).

2. Description of Related Art 2,2-Difluoroethanol is an important intermediate in the synthesis of active agrochemical and pharmaceutical ingredients. There are various known processes for preparation of fluorinated alcohols. Many of the processes proceed via catalytic hydrogenation or through use of reducing agents.

Henne et al. describe, for example, in *J. Am. Chem. Soc.* 1952, 74, 1426-1428, the reduction of a difluoroacetyl chloride formed in situ by lithium aluminium hydride to obtain difluoroethanol in 69% yield. An economic disadvantage is the stoichiometric use of expensive hydride sources.

Booth et al. describe, in *Tetrahedron* 1990, 46, 2097-2110, the reduction of difluoroacetic acid with borane-dimethyl sulphide complex to obtain difluoroethanol in 55% yield.

EP-1 820 789 A1 describes the reduction of fluorinated carboxylic acids, carbonyl halides or carboxylic esters with hydrogen in the presence of a catalyst. The method described therein is said to be especially suitable for preparation of difluoroethanol ($CF_2HCH_2OH$), preferably proceeding from fluorinated esters, especially from methyl or ethyl difluoroacetate. The reaction takes place under elevated pressure, and the catalyst used is iridium, rhodium or ruthenium on charcoal. The publication states that, proceeding from methyl difluoroacetate, the desired difluoroethanol was obtained in a yield of 74.4% by catalytic hydrogenation using an Rh/C catalyst after 18 hours at 40 bar. One disadvantage of this process is the use of an expensive noble metal catalyst, and another is that the reaction is executed at high pressure, which has the consequence that the reaction has to be performed in specific high-pressure apparatuses.

WO 2007/071841, which is concerned with the preparation of difluoroethanol, uses, as the starting material for a (triple) catalytic hydrogenation, a compound $CF_2XC(O)X$ where Hal is Cl, Br or iodine (especially chlorodifluoroacetyl chloride). The catalysts used are especially ruthenium, rhodium, palladium, osmium, iridium and platinum, which have been applied to a support. The support should likewise have the function of a Lewis acid and especially contain aluminium ions (e.g. zeolites or montmorillonite). The reaction can take place in the gas phase, and in that case preferably at a temperature of 200 to 300° C. and a hydrogen pressure of preferably 1 to 5 bar. The reaction can likewise take place in the liquid phase, in which case the reaction temperature is between 40 and 70° C. The hydrogen pressure is preferably between 10 and 20 bar. The reaction in the gas phase is emphasised as advantageous since it gave better yields of difluoroethanol and a higher conversion rate.

WO 2009/040367 describes a process for preparing 2,2-difluoroethanol. For this purpose, in a first stage, 1-brom-2,2-difluoroethane is prepared proceeding from difluorovinylidene. In a second stage, the compound is reacted with an oxygen nucleophile, for example sodium or potassium salts of acetic or formic acid. WO 2009/040367 also states that the bromine atom in 1-bromo-2,2-difluoroethane is activated by reaction with magnesium, zinc, lithium or copper (especially NaI or KI) prior to reaction with the oxygen nucleophile.

More specifically, WO2009/040367 describes the preparation of difluoroethanol by, in stage 2, reacting difluorobromoethane with sodium acetate (=sodium salt of acetic acid) in the presence of potassium iodide, by heating to 130° C. in DMF for 18 h, followed by a base-catalysed transesterification in the presence of methanol. The difluoroethyl acetate formed can first be isolated by distillation in an intermediate step or converted directly to difluoroethanol. Proceeding from difluorobromoethane used, the yields are between 56.8 and 87%. The process described here is complex and relatively costly and requires many intermediate steps to arrive at the desired difluoroethanol. If only step 2 is to be performed, the expensive difluorobromoethane has to be purchased.

Japanese Publication JP 62-273925A (=JP 1987-273925A) describes the preparation of 2,2-difluoroethanol proceeding from 1-chloro-2,2-difluoroethane with butyrolactone in the presence of water and potassium hydroxide. For this purpose, the reaction mixture is heated to 200° C. in autoclave for 2.5 h, giving 2,2-difluoroethanol in only 48.6% yield at 86% conversion of the difluorochloroethane.

None of the aforementioned processes for preparation of 2,2-difluoroethanol are optimal. Many of the processes use expensive catalysts and it is necessary to work under pressure, which is always associated with a high level of complexity on the industrial scale. Other processes (for example that from WO 2009/040367) consist of several process steps, proceed via the expensive 1-bromodifluoroethane, which also has to be activated for better reaction, or use the cheaper 1-chloro-2,2-difluoroethane, in which the yield and selectivity of 48.6% achieved at 86% conversion of the difluorochloroethane is only very low, which is attributable to the use of the unreactive 1-chloro-2,2-difluoroethane.

SUMMARY

Proceeding from the known processes, the problem addressed was thus that of providing a process for preparing 2,2-difluorethanol, which is simple and inexpensive, which uses a compound which is commercially available at comparatively favourable cost as the starting compound, and with which 2,2-difluoroethanol is obtained in high yield and good purity. It is equally desirable to provide a process which requires a small number of reaction steps and which needs substantially no reaction auxiliaries and, if possible, need not be conducted in a pressure vessel.

The inventors have now found that, surprisingly, 1-chloro-2,2-difluoroethane can be converted in a simple manner in a nucleophilic substitution reaction to a difluoroethyl carboxylate, which then reacts further through base-catalysed transesterification in the presence of an alcohol to give 2,2-difluoroethane.

This is surprising in that it is common knowledge that alkyl chlorides in nucleophilic substitution reactions have a much lower reactivity than the corresponding alkyl bromides and iodides (March, *Advanced Organic Chemistry* 5th Edition, chapter 10, John Wiley & Sons, New York 2001). The low yields from JP 62-273925 demonstrate this.

It is also surprising in that the process according to the invention can be executed in standard reaction vessels, even though 1-chloro-2,2-difluoroethane has a boiling point of only 35° C. and is thus volatile. In order to achieve a sufficiently high conversion rate in the case of volatile substances, the reaction has to be conducted at elevated temperatures and under pressure.

The application thus relates to a process for preparing 2,2-difluoroethanol, comprising the following steps:

step (i): reacting 1-chloro-2,2-difluoroethane with an alkali metal salt of formic acid or acetic acid in a suitable solvent to give the corresponding 2,2-difluoroethyl formate or 2,2-difluoroethyl acetate, characterized in that 1-chloro-2,2-difluoroethane is added gradually to a mixture, heated to the desired reaction temperature, of solvent and alkali metal salt of formic acid or acetic acid;

step (ii): transesterifying the 2,2-difluoroethyl formate or 2,2-difluoroethyl acetate from step (i) in the presence of an alcohol (preferably methanol) and optionally of a base.

The reaction can be represented as follows:

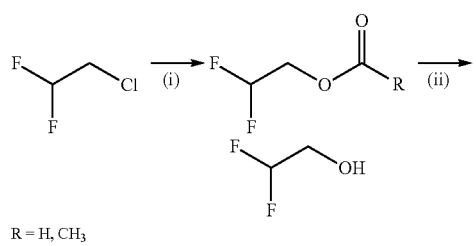

R = H, CH$_3$

DETAILED DESCRIPTION OF A PREFERRED EMBODIMENT

The use of 1-chloro-2,2-difluoroethane has the advantage that it is cheaper than 1-bromo-2,2-difluoroethane and is additionally obtainable commercially in relatively large amounts.

The gradual addition of 1-chloro-2,2-difluoroethane to the heated mixture of the alkali metal salt of formic acid or acetic acid and solvent achieves complete and simple conversion to the desired product without any need to work under elevated pressure and without needing to use reaction auxiliaries (for example catalysts, additives). The reaction time is likewise comparatively short. This has the advantage that the reaction can be performed in a simple and inexpensive manner, and that it is additionally environmentally friendly since it is does not require any auxiliary chemicals.

According to the invention, the expression "gradual addition" is understood to mean the addition of 1-chloro-2,2-difluoroethane in portions or dropwise over a prolonged period. The length of the period is guided by the size of the reaction batch, and thus by the amount of 1-chloro-2,2-difluoroethane to be added, and can be determined by the person skilled in the art by routine methods. It is crucial that the 1-chloro-2,2-difluoroethane added gradually has enough time to react with the alkali metal salt of formic acid or acetic acid. The reaction time for step (i) in the process according to the invention is accordingly selected such that full conversion of 1-chloro-2,2-difluoroethane is ensured. The reaction time may be in the range from 0.1 to 12 h. The reaction system is preferably adjusted such that the reaction time is in the range from 0.25 to 5 h and more preferably in the range from 0.5 to 2 or 3 h.

In step (i) of the process according to the invention, preference is given to using sodium acetate or potassium acetate, or sodium formate or potassium formate, particular preference being given to using potassium acetate or potassium formate.

The alkali metal salt of formic acid or acetic acid used in step (i) is used in an about 1- to about 10-fold molar excess, preferably in an about 1- to about 2-fold molar excess, and more preferably in a 1.1- to 1.5-fold molar excess, based on the 1-chloro-2,2-difluoroethane used.

The solvent used in the process according to the invention is preferably used in such an amount that the stirrability of the reaction mixture remains good over the whole process. Advantageously, based on the 2.2-difluoro-1-chloroethane used, 1 to 50 times the amount of solvent (v/v), preferably 2 to 40 times the amount of solvent (v/v), and more preferably 2 to 20 times the amount of solvent (v/v) is used.

Inventive solvents in step (i) are especially organic solvents (alone or as a mixture with other organic solvents) which have a boiling point above 70° C. and are inert under the reaction conditions. Preferred solvents for use in step (i) are dimethyl sulphoxide, tetramethylene sulphoxide, dipropyl sulphoxide, benzyl methyl sulphoxide, diisobutyl sulphoxide, dibutyl sulphoxide, diisoamyl sulphoxide; N,N-dimethylacetamide, N-methylformamide, N,N-dimethylformamide, N,N-dipropylformamide, N,N-dibutylformamide, N,N-methylpyrrolidone, N-methylcaprolactam and mixtures thereof, particular preference being given to N,N-dimethylacetamide, N-methylpyrrolidone, N,N-dimethylformamide, dimethyl sulphoxide, tetramethylene sulphoxide and mixtures thereof, very particular preference being given to dimethyl sulphoxide or N-methylpyrrolidone and mixtures thereof.

The gradual addition in step (i) of the process according to the invention is effected at the desired reaction temperature, reaction temperature being understood to mean the internal temperature. The reaction temperature is usually in the range from 70° C. to 200° C., preferably in the range from 80° C. to 160° C. and more preferably in the range from 90° C. to 150° C.

The process according to the invention is in principle performed under standard pressure. However, it can alternatively also be performed in a pressure-stable closed experimental vessel (autoclave). In that case, the pressure during the reaction (i.e. the autogenous pressure) depends on the reaction temperature used, the solvent used and the amount of reactants used. If a pressure increase is desired, an additional pressure increase can be performed by means of addition of an inert gas, such as nitrogen or argon.

Step (i) in the process according to the invention is in principle performed in the absence of a reaction auxiliary (e.g. catalysts or additives). It is possible from a chemical point of view to activate 1-chloro-2,2-difluoroethane by adding a reaction auxiliary/catalyst to the mixture of alkali metal salt of formic acid or acetic acid and solvent. It is conceivable to use alkali metal iodides and bromides (e.g. sodium iodide, potassium iodide, sodium bromide or potassium bromide). It would likewise be possible to use quaternary ammonium salts of the NR$_4$$^+$X$^-$ form in which R is C$_{1-12}$-alkyl and X is Br or I (e.g. tetrabutylammonium bromide, tetrabutylammonium iodide and tricaprylmethylammonium bromide). Posssible concentrations of the catalysts are in the range from 0.001 to 0.1 equivalent based on the 1-chloro-2.2-difluoroethane used.

The transesterification in step (ii) is base-catalysed. Step (ii) can be performed with the reaction mixture from step (i), i.e. without isolating the 2,2-difluoroethyl formate or 2,2-difluoroethyl acetate prepared in step (i), in which case there is no need to add a base to the reaction mixture since it is already present in the reaction mixture (for example alkali metal salt of formic acid or acetic acid from step (i)). It is preferable to use the reaction mixture from step (i) in step (ii) without a further isolation step.

It will be appreciated that it is also possible to use isolated 2,2-difluoroethyl formate or 2,2-difluoroethyl acetate in step (ii). For this purpose, the reaction mixture obtained after step (i) can be worked up, and 2,2-difluorethyl formate or 2,2-difluoroethyl acetate can be isolated. These esters can also be removed by distillation. If the 2,2-difluoroethyl formate or 2,2-difluoroethyl acetate obtained in step (i) is isolated after step (i), a base has to be added in step (ii).

Step (ii) is usually effected in substance, i.e. without addition of (further) solvents, in which case the alcohol used in step (ii) serves as the solvent.

The transesterification is effected by addition to the reaction mixture from step (i) or to the isolated ester, optionally the base and the alcohol. Particularly in the case of use of the isolated ester, the addition of a solvent is dispensed with. The mixture thus obtained is stirred at room temperature or under reflux conditions for 0.5 to 2 h.

Alcohols which are usable in step (ii) and can simultaneously serve as solvents are methanol, butanol, isobutanol, pentanol and isomers thereof, hexanol and isomers thereof, preference being given to using methanol. The alcohol is used in a 1- to 40-fold excess, preferably in a 1.5- to 10-fold excess and more preferably in a 2- to 5-fold excess.

Examples of the inventive bases required in step (ii) are alkali metal hydroxides, and alkali metal methoxide in solid form or as a solution in methanol, alkali metal carbonates, alkali metal acetates, alkali metal formates and alkali metal phosphates. Preferred bases are sodium methoxide, sodium hydroxide and potassium acetate. The amount of base added is 0.001 to 0.1 equivalent based on the 2,2-difluoroethyl formate or 2,2-difluoroethyl acetate used.

The 2,2-difluoroethanol is worked up (purified) by distillation.

The present invention is illustrated in detail by the examples which follow, though the examples should not be interpreted in such a manner as to restrict the invention.

Example 1

Step (i): Preparation of 2,2-difluoroethyl Acetate

A three-neck flask with mechanical stirrer, dropping funnel and dry ice condenser is initially charged with 148 g (1.475 mol) of potassium acetate in 300 ml of dimethyl sulphoxide, which are heated to 120° C. Subsequently, a mixture of 100 g (0.983 mol) of 2,2-difluoro-1-chloroethane in 100 ml of dimethyl sulphoxide is added dropwise within one hour. The reaction mixture is stirred at 120° C. for a further 1.5 h and cooled to room temperature. Reaction monitoring by means of gas chromatography shows complete conversion of the 2,2-difluoro-1 chloroethane. After distillation, the desired 2,2-difluoroethyl acetate is obtained in 90.8% yield.

NMR $^1$H (CDCl$_3$): 5.94 (tt, 1H, J=3.9 Hz, 55.1 Hz), 4.27 (dt, 2H, J=4.0 Hz, 13.7 Hz), 2.14 (s, 3H)
NMR $^{19}$F (CDCl$_3$): −126.24 (td, J=13.7 Hz, 55.1 Hz)

Step (ii): Preparation of 2,2-difluoroethanol from 2,2-difluoroethyl Acetate

In a three-neck flask with mechanical stirrer and reflux condenser, 112 g (889 mmol) of 2,2-difluoroethyl acetate are admixed with 100 g (3.11 mol) of methanol, and 2.14 g (53 mmol) of solid sodium hydroxide are added. The reaction mixture is stirred at room temperature for 1 h. Reaction monitoring by means of gas chromatography shows complete conversion of the starting material. After distillation, the target product is obtained in 74.4% yield.

NMR $^1$H (CDCl$_3$): 5.85 (tt, 1H, J=3.9 Hz, 55.8 Hz), 3.84–3.78 (m, 2H), 2.02 (br t, 1H, J=6.7 Hz)
NMR $^{19}$F (CDCl$_3$): −128.3 (td, J=14.4 Hz, 55.8 Hz)

Example 2

Without Isolation of 2,2-difluoroethyl Acetate

Step (i): A three-neck flask with mechanical stirrer, dropping funnel and dry ice condenser is initially charged with 289.5 g (2.95 mol) of potassium acetate in 600 ml of dimethyl sulphoxide, which are heated to 120° C., and then a mixture of 200 g (1.97 mol) of 2,2-difluoro-1-chloroethane in 200 ml of dimethyl sulphoxide is added dropwise within 30 minutes. The reaction mixture is stirred for a further 2 h and cooled to 60° C. Reaction monitoring by means of gas chromatography shows complete conversion of the 2,2-difluoro-1-chloroethane.

Step (ii): 221 g (6.88 mol) of methanol are added dropwise within 20 minutes and then the reaction mixture is heated to 90° C. for 2 h.

Reaction monitoring by means of gas chromatography showed complete conversion of the 2,2-difluoroethyl acetate. After distillation, the 2,2-difluoroethanol is obtained in 84.4% yield.

NMR $^1$H (CDCl$_3$): 5.85 (tt, 1H, J=3.9 Hz, 55.8 Hz), 3.84–3.78 (m, 2H), 2.02 (br t, 1H, J=6.7 Hz)
NMR $^{19}$F (CDCl$_3$): −128.3 (td, J=14.4 Hz, 55.8 Hz)

The invention claimed is:

1. A process for preparing 2,2-difluoroethanol, comprising:
   (i): reacting 1-chloro-2,2-difluoroethane with an alkali metal salt of formic acid or acetic acid in a suitable solvent to give the corresponding 2,2-difluoroethyl formate or 2,2-difluoroethyl acetate, wherein, 1-chloro-2,2-difluoroethane is added gradually to a mixture, heated to a desired reaction temperature, of solvent and alkali metal salt of formic acid or acetic acid;
   (ii): transesterifying the 2,2-difluoroethyl formate or 2,2-difluoroethyl acetate from
   (i): in the presence of an alcohol and optionally of a base.

2. The process according to claim 1, wherein the suitable solvent is at least one selected from the group consisting of dimethyl sulphoxide, tetramethylene sulphoxide, dipropyl sulphoxide, benzyl methyl sulphoxide, diisobutyl sulphoxide, dibutyl sulphoxide, diisoamyl sulphoxide; N,N-dimethylacetamide, N-methylformamide, N,N-dimethylformamide, N,N-dipropylformamide, N,N-dibutylformamide, N-methylpyrrolidone, and N-methylcaprolactam.

3. The process according to claim 1, wherein the reaction temperature in (i) in which the 1-chloro-2,2-difluoroethane is added is in the range from 70° C. to 200° C.

4. The process according to claim 1, wherein gradual addition is understood to mean addition in portions and/or dropwise.

5. The process according to claim 1, wherein 2,2-difluoroethyl formate and/or 2,2-difluoroethyl acetate is separated from the reaction mixture by distillation after (i), and wherein a base is added in (ii).

6. The process according to claim 5, wherein the base is selected from the group consisting of alkali metal hydroxides, alkali metal methoxides, alkali metal carbonates, alkali metal acetates, alkali metal formates and alkali metal phosphates.

7. The process according to claim 1, wherein the reaction mixture from (i) is used in (ii) without further purification and/or an isolation step, in which case no base is added in (ii).

8. The process according to claim 1, wherein the alcohol is methanol.

9. The process according to claim 1, wherein the alkali metal salt is sodium acetate or potassium acetate.

10. The process according to claim 1, wherein the alkali metal salt is sodium formate or potassium formate.

11. The process according to claim 1, wherein the base is used in step (ii).

12. The process according to claim 11, wherein the base is sodium methoxide, sodium hydroxide, or potassium acetate.

13. The process according to claim 1, wherein the reaction time of (i) is from 0.5 to 3 hours.

* * * * *